(12) United States Patent
Ishikawa

(10) Patent No.: US 6,758,952 B2
(45) Date of Patent: Jul. 6, 2004

(54) GAS SENSOR

(75) Inventor: Satoshi Ishikawa, Nagoya (JP)

(73) Assignee: NGK Spark Plug Co., Ltd., Aichi (JP)

(*) Notice: Subject to any disclaimer, the term of this patent is extended or adjusted under 35 U.S.C. 154(b) by 0 days.

(21) Appl. No.: 10/347,188

(22) Filed: Jan. 21, 2003

(65) Prior Publication Data

US 2003/0136675 A1 Jul. 24, 2003

(30) Foreign Application Priority Data

Jan. 21, 2002 (JP) ........................................ 2002-011442

(51) Int. Cl.[7] ........................................... G01N 27/409
(52) U.S. Cl. ..................................... 204/424; 204/427
(58) Field of Search ................................ 304/421–429

(56) References Cited

U.S. PATENT DOCUMENTS 5,900,129 A    5/1999  Tsuji et al.

FOREIGN PATENT DOCUMENTS

| JP | 2000-193632 | 7/2000 |
|---|---|---|
| JP | 2000-249678 | 9/2000 |
| JP | 2001-208724 | 8/2001 |
| JP | 2001-235445 | 8/2001 |

*Primary Examiner*—Kaj K. Olsen
(74) *Attorney, Agent, or Firm*—Sughrue Mion, PLLC

(57) ABSTRACT

An oxygen sensor as a gas sensor has a vent hole for taking an atmosphere into an outer sleeve in an outer sleeve cover for covering the outer sleeve from above and manufactured by rubber. A filter unit made by a tubular member enlarged in diameter on a predetermined boundary, a sheet-shaped filter having a water repellent property and an oil repellent property, and an O-ring is fitted and inserted into this vent hole. The upper end portion of a large diameter portion is folded by bending processing. Folding portion nips and supports the filter and the O-ring between the folding portion and a step portion formed between a large diameter portion and a small diameter portion. It is sufficient to set the size of a filter to same size as the vent hole. The filter can be attached to a predetermined position of the outer sleeve cover.

12 Claims, 11 Drawing Sheets

GAS SENSOR

BACKGROUND OF THE INVENTION

1. Field of the Invention

The present invention relates to a gas sensor having a detecting element having a pair of electrodes formed on a surface of a solid electrolytic body of an oxygen ion conductive property, and measuring the concentration of a measured gas.

2. Description of the Related Art

Various kinds of gas sensors such as an HC sensor, a NOx sensor, etc. are conventionally known as a gas sensor for detecting a concentration of a specific gas component from a mixing gas. An oxygen sensor having a detecting element made by a solid electrolytic body of an oxygen ion conductive property is known as one of these gas sensors.

As shown in FIG. 10, a detecting element 102 of a general oxygen sensor 101 is made such that an inside electrode 102a and an outside electrode 102b are formed on an inner and outer surfaces of a cylindrical body having a bottom. A tip side of the cylindrical body is covered by the solid electrolytic body. A rear end side of the cylindrical body is opened by the solid electrolytic body.

The oxygen sensor 101 detects an oxygen concentration of a measured gas by electromotive force caused between electrodes by a concentration difference between the measured gas outside the detecting element 102 and an atmosphere as a reference gas filling an internal space 102c of the cylindrical body.

In the oxygen sensor 101 for detecting the oxygen concentration of the measured gas by such a principle, the detecting element 102 is held by a metal shell 111 such that the tip portion of the detecting element 102 is exposed to the measured gas from the tip side of a through hole 112 formed in the axial direction of the metal shell The detecting element is covered with an outer sleeve 113 so as to protect the detecting element from dust, water, oil, flied stones, etc. therearound.

In the oxygen sensor 101, a rear end opening portion of the outer sleeve 113 is covered by an outer sleeve cover 130 as a seal member manufactured by rubber.

However, in a perfect covering state, no sufficient atmosphere (reference gas) can be sent into the internal space 102c of the detecting element 102 stored into the oxygen sensor 101. Accordingly, it is known that a vent hole 131 is arranged in the outer sleeve cover 130 of the oxygen sensor 101 of this kind.

A filter 153 has a permeable property and a water repellent property to selectively introduce the atmosphere into the outer sleeve 113 while preventing the invasion of water into the outer sleeve 113. The filter 153 is arranged in this vent hole 131 so as to block the vent hole 131 (e.g., see patent literatures 1 and 2).

[Patent Literature 1]
   JP-A-2000-193632 (see FIG. 3)

[Patent Literature 2]
   JP-A-2001-208724 (see FIG. 1)

In the oxygen sensors described in the above patent literatures, a vent hole is covered by a filter by fixing the filter using another member such that the filter comes in contact with an entire inner face of the vent hole. Therefore, there are cases in which manufacture cost of the sensor is raised and the filter is damaged in a manufacture process of the sensor.

Namely, in the oxygen sensors described in the above patent literatures, as shown in FIG. 11, a sleeve-shaped insertion member 151 is covered with a sheet-shaped filter 153, and this filter 153 is pushed into the vent hole 131 from forward (the side of a metal shell).

Thus, the vent hole 131 is covered by the filter 153 while the filter 153 comes in contact with the inner face of the vent hole 131. Therefore, in the pushing process of the insertion member 151 into the vent hole 131, there is a case in which the filter 153 is pulled in the direction opposed to the insertion direction so that the filter 153 is broken.

When the vent hole 131 is covered by the filter 153 in such a method, the filter 153 is arranged outside the insertion member 151, and is fixedly nipped and supported between the inner face of the vent hole 131 and the outer circumferential face of the insertion member 151 in design. Accordingly, the filter 153 of a size sufficiently greater than the diameter of the vent hole 131 must be prepared. Therefore, manufacture cost is raised and there are many useless portions.

SUMMARY OF THE INVENTION

It is an object of the present invention is to provide a gas sensor capable of attaching a filter to a vent hole simply and with a low cost.

To achieve such an object, a gas sensor comprising a detecting element having a pair of electrodes formed on the surface of a solid electrolytic body of an oxygen ion conductive property; a metal shell having a through hole formed in the axial direction and holding the detecting element within the through hole so as to expose the tip portion of the detecting element to a measured gas from the tip side of this through hole; an outer sleeve arranged on the rear end side of the metal shell and internally accommodating the detecting element; and an outer sleeve cover fitted and inserted in a rear end opening portion of this outer sleeve and extended from its own rear end face to the tip face, and having a vent hole as a circulating path of a gas of the interior and the exterior of the outer sleeve. A filter unit formed by a body separated from a gas sensor main body is arranged in the gas sensor.

The filter unit has a tubular member fitted and inserted into the vent hole of the outer sleeve cover, and a filter arranged inside this tubular member and fixed on the inside of this tubular member and having a permeable property and a water repellent property. The filter unit has such that the filter unit is fitted and inserted in the vent hole of the outer sleeve cover and the vent hole is covered by the filter.

In the gas sensor made in this way, the filter unit for fixing the filter inside (interior) the tubular member is used. Accordingly, if this filter unit is fitted and inserted into the vent hole of the outer sleeve cover, the vent hole can be simply covered by the filter. In other words, in the present invention, the gas sensor can be simply made by attaching the filter unit to the vent hole such that a gas can be circulated in the interior and the exterior of the outer sleeve while the invasion of a waterdrop, dust, etc. into the outer sleeve from the vent hole is prevented by the function of the filter. The productivity of a product can be improved in the gas sensor of the present invention.

The conventional gas sensor adopts the method for mounting the filter to the outer sleeve cover so as to set the filter to the exterior of an insertion member and directly push the filter into the vent hole. Therefore, there is a case in which the filter is damaged during the insertion. However, in the present invention, since the filter is mounted to the inside of the tubular member in advance, no filter is damaged when the filter unit is fitted and inserted. Accordingly, in the gas sensor of the present invention, manufacture cost of the product can be restrained and reliability of the filter, therefore, reliability of the gas sensor can be improved.

When the filter unit includes a separate body in this way and the filter unit is simply fitted, inserted and attached to the outer sleeve cover, there is a possibility that the filter unit gets out of the vent hole by vibrating the gas sensor after the attachment. Accordingly, for example, the filter unit is preferably fixed to the outer sleeve cover by an adhesive, etc. so as to prevent the filter unit from getting out of the outer sleeve cover.

However, performance of the adhesive is reduced when time has passed. Therefore, there is a possibility that no filter unit can be firmly fixed to the outer sleeve cover for a long period.

Therefore, in the gas sensor, a first engaging portion engaged with the tip portion (metal shell side) of the outer sleeve cover, and a second engaging portion engaged with the rear end portion (the side opposed to the metal shell) of the outer sleeve cover are preferably arranged in the tubular member.

In the gas sensor, the filter unit is fixed to the outer sleeve cover such that the outer sleeve cover is nipped by the first and second engaging portions from both opening portion sides of the vent hole. Therefore, the extraction of the filter unit can be reliably prevented in comparison with the case using the adhesive, etc.

In particular, the filter may be fixed to the tubular member so as to be arranged on the rear end side from the vent hole of the outer sleeve cover.

In other words, the filter may be fixed to the tubular member to be projecting form the rear end face of the outer sleeve cover. The filter upper face (a face located on the rear end side of the gas sensor) is located on the backward side from the rear end face (a face located on the side opposed to the metal shell) of the outer sleeve cover by arranging the filter on the rear end side from the vent hole of the outer sleeve cover in this way.

Therefore, when the gas sensor is used, it is possible to effectively restrain that water is collected and dust is accumulated on the filter upper face.

However, when the filter is fixed to the tubular member so as to be arranged on the rear end side from the vent hole of the outer sleeve cover, it is possible to restrain water from being collected on the filter upper face, but the danger of damage of the filter due to flied stones is increased. Therefore, the filter may be also fixed to the tubular member so as to be arranged within the vent hole of the outer sleeve cover. The filter upper face is located on the forward side from the rear end face of the outer sleeve cover by arranging the filter within the vent hole of the outer sleeve cover in this way. Therefore, it is possible to effectively prevent flied stones, etc. from hitting against the filter so that the damage of the filter can be effectively restrained.

However, when the filter is arranged within the vent hole of the outer sleeve cover, the damage of the filter due to flied stones, etc. can be restrained, but there is a fear that water, etc. are collected on the filter upper face as mentioned above. Therefore, a construction of of a gas sensor is used for solving both the problem of collecting water, etc. on the filter upper face, and the problem of damaging the filter by flied stones, etc. In this construction, while the construction for fixing the filter to the tubular member so as to be arranged within the vent hole of the outer sleeve cover is set to a premise, a groove portion having one end side communicated with the vent hole and the other end side opened to the side wall face of the outer sleeve cover is formed on the rear end face of the outer sleeve cover, and the filter is arranged on the rear end side from a deepest portion of the groove portion.

Namely, in the gas sensor of the present invention, the damage of the filter due to flied stones, etc. can be prevented since the rear end face of the outer sleeve cover is located in a position higher than that of the filter as mentioned above by arranging the filter within the vent hole of the outer sleeve cover. In addition, in the gas sensor of the present invention, the groove portion having one end side (inside) communicated with the vent hole and the other end side (outside) opened to the side wall face of the outer sleeve cover is formed on the rear end face of the outer sleeve cover, and the filter is arranged on the rear end side from the deepest portion of this groove portion. In other words, the filter is disposed between a deepest portion of the groove portion and the rear end face of the outer sleeve cover.

Accordingly, even when water is splashed on the filter, this water can be discharged to the diametrical outside of the outer sleeve cover through the groove portion located in a position lower that that of the filter. Namely, it is possible to simultaneously solve both the problem of collecting water, etc. on the filter upper face and the problem of damaging the filter by flied stones, etc. by arranging the deepest portion of the above groove portion in a low position while the rear end face of the outer sleeve cover is arranged in a high position with the filter as a reference. The shape of the groove portion is not particularly limited, but can be formed in a U-shape and a V-shape in section.

With respect to the above groove portion, it is preferable that the outer sleeve cover has plural through holes for a lead wire for inserting the lead wire electrically connected to the detecting element, and the plural groove portions are formed on the rear end face of the outer sleeve cover in positions not interfering with the through holes for the lead wire. In other words, the groove portion is formed on the rear end face of the outer sleeve cover except for where the through holes for the lead wire are formed.

Namely, water, etc. splashed on the filter upper face can be efficiently discharged toward the diametrical outside of the outer sleeve cover through the groove portion by forming the groove portion by effectively practically utilizing the limited accumulation of the outer sleeve cover.

A filter also having an oil repellent property is preferably used as the filter.

The filter of a water repellent property is used as the above filter to water-tightly block the vent hole. However, when the oil is attached to the filter of the water repellent property, this water repellent property cannot be sufficiently shown. In consideration of such a problem, the oil repellent property is provided by performing oil repellent processing, etc. in the filter in the gas sensor. In particular, there is a possibility that the gas sensor for a vehicle, etc. is polluted by the oil. Accordingly, if the filter of the oil repellent property is used in the filter unit in this way, performance of the filter unit can be maintained for a long period.

In the gas sensor of the present invention, the filter unit is preferably made such that plural filters are fixed to the inside of the tubular member. If a filter set to be arranged in an outermost layer is broken, waterproof property can be maintained by the other filters by arranging the plural filters inside the tubular member in this way. When the plural filters are arranged inside the tubular member, the plural filters can be overlapped or arranged at a predetermined interval with respect to the central axis direction of the tubular member.

Further, in the gas sensor of the present invention, the filter unit is preferably made such that a partition plate having plural opening portions for exposing the filter is fixed to the rear end side from the filter inside the tubular member. Since the partition plate having the plural opening portions is arranged on the rear end side (in other words, the filter upper face) of the filter in this way, the atmosphere can be introduced into the outer sleeve while the damage of the filter due to flied stones, etc. can be effectively prevented.

In addition to this, a seal member for water-tightly fixing the filter inside the tubular member is preferably arranged within the filter unit to water-tightly hold the interior of the filter unit.

If the filter unit having such a seal member is fitted and inserted into the vent hole of the gas sensor, it is possible to sufficiently restrain that a waterdrop, etc. are invaded into the filter unit through the gap between the filter and the tubular member, and the interior of the outer sleeve is polluted by the waterdrop, etc. As a result, the performance of the gas sensor can be maintained for a long period. The seal member may be an adhesive able to adhere the filter outer edge to the inner wall of the tubular member, and may be also a seal member such as an O-ring manufactured by rubber. In particular, when the seal member manufactured by rubber is used, the rubber is adhered to the inner wall of the tubular member in the application of heat so that it is effective to take an airtight measure within the gas sensor.

If productivity of the filter unit is considered, the gas sensor is preferably made so that a filter fixing portion for fixing the filter in a predetermined position inside the tubular member is arranged in the tubular member. The filter unit is made such that the filter and an O-ring as the seal member are fixedly nipped and supported between the filter fixing portion and an end portion of the tubular member folded in the inside direction of the tubular member.

In the gas sensor of such a construction, the O-ring and the filter are stored to the filter fixing portion formed inside the tubular member so as to be overlapped, and the end portion of the tubular member is then folded by bending processing, etc. in the inside direction of this tubular member so that the filter unit can be completed. Accordingly, the filter unit can be simply and efficiently manufactured.

In the gas sensor, a step portion as the above filter fixing portion is formed in the inner wall of the tubular member by enlarging the tubular member in diameter on a predetermined boundary. The O-ring and the filter are arranged on one end side of the tubular member enlarged in diameter so as to be overlapped with the above step portion, and the O-ring and the filter are stored inside the tubular member.

Further, in the gas sensor, the O-ring and the filter are nipped and supported between the step portion as the filter fixing portion and the end portion of the tubular member by folding the end portion of the tubular member on one end side in the inside direction of the tubular member. Thus, the filter unit is made so as to fix the O-ring and the filter.

When the method for forming the step portion by the diameter enlargement of the tubular member in this way is adopted, the filter fixing portion can be simply formed inside the tubular member.

Further, when the step portion is formed in the tubular member by the diameter enlargement, the first or second engaging portion can be formed in the outer wall of the tubular member corresponding to the step portion. Accordingly, the number of processes at the manufacturing time of the filter unit can be reduced, and productivity of the filter unit can be improved.

DESCRIPTION OF THE PREFERRED EMBODIMENTS

The embodiments of the present invention will next be explained together with the drawings.

Figure 1:
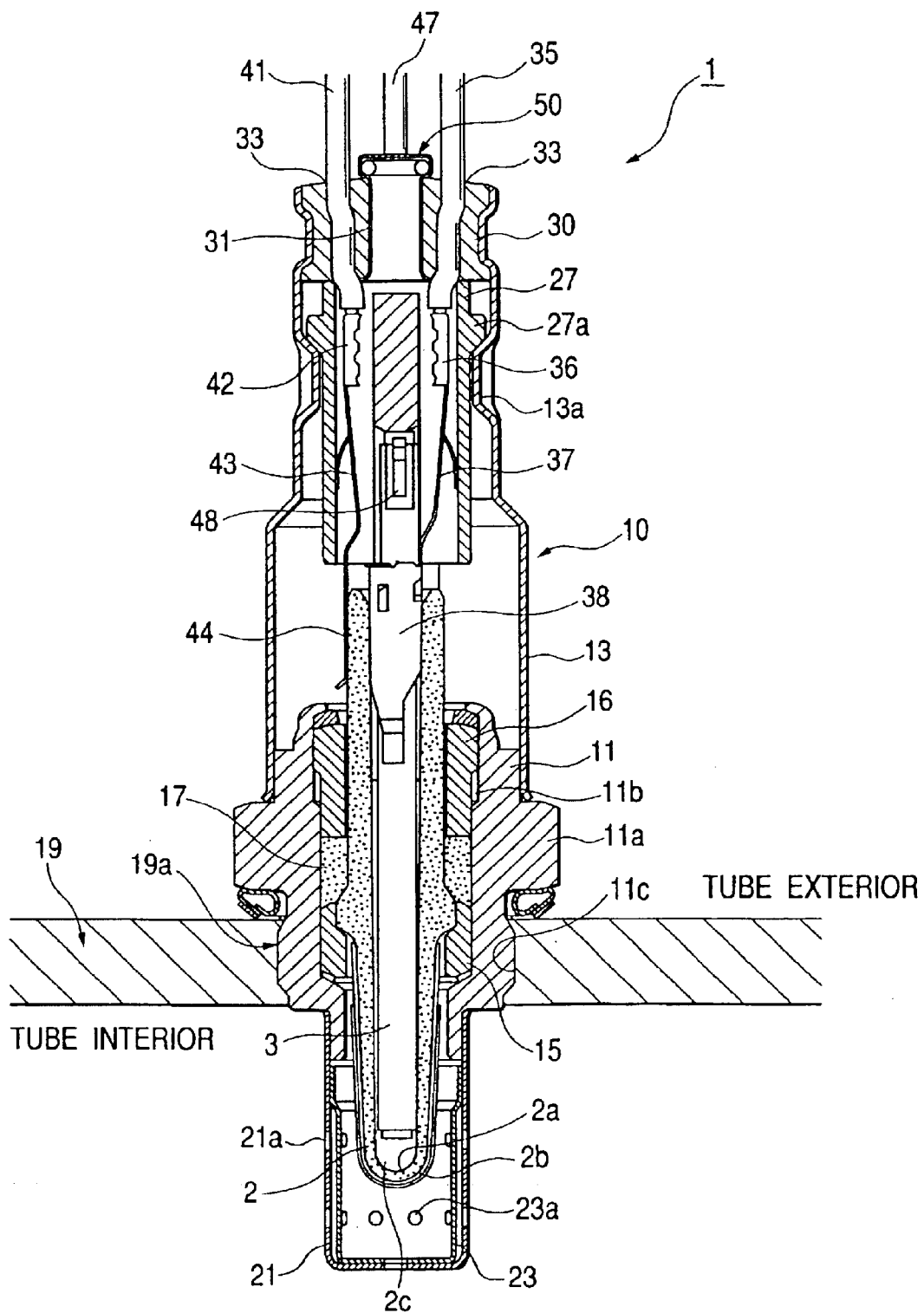
FIG. 1 is a schematic sectional view showing a construction of an oxygen sensor 1 of a first embodiment.

FIG. 1 is a schematic sectional view showing the construction of an oxygen sensor 1 of a first embodiment applying the present invention thereto.

As shown in FIG. 1, the oxygen sensor 1 of the first embodiment as one of gas sensors includes a detecting element 2, a ceramic heater 3 for operating the detecting element 2 at a suitable temperature, a casing 10 for accommodating each portion of the sensor on the inside, etc.

The detecting element 2 is formed in a hollow shaft shape in which the tip of the detecting element 2 is closed by a solid electrolytic body of an oxygen ion conductive property with $ZrO_2$ as a main component.

Further, the detecting element 2 includes a pair of porous electrode layers (an inside electrode 2a and an outside electrode 2b) made by platinum (Pt). The pair of porous electrode layers are formed on the inner and outer faces.

The ceramic heater 3 is formed in a shaft shape. The ceramic heater 3 is arranged in an internal space 2c of the detecting element 2.

On the other hand, the casing 10 includes a metal shell 11 for holding the detecting element 2 and an outer sleeve 13 for protecting the sensor interior including the detecting element 2, etc.

The metal shell 11 is formed in a hollow shape opened in its both end portions. The metal shell 11 includes a convex step portion 11a, which is arranged in a central side wall of the metal shell 11.

Further, the metal shell 11 has a through hole 11b, which is formed in the axial direction. The closed tip portion of the detecting element 2 is projected from the tip side of this through hole 11b such that this closed tip portion is exposed to a measured gas filling a tube described later.

Further, the detecting element 2 is held within the through hole 11b such that the rear end portion of the detecting element 2 is projected from the rear end side of the through hole 11b.

Namely, the detecting element 2 is held in a state in which the outer circumference of the detecting element 2 near the central portion in the axial direction is electrically insulated through ceramic holders 15, 16 formed by insulating ceramic with respect to the metal shell 11, and ceramic powder 17 formed by talc.

An attaching screw portion 11c capable of being screwed into an attaching hole 19a is formed in the outer circumference of the metal shell 11.

The attaching hole 19a is formed on the wall face of a pipe 19 such as an exhaust pipe, etc., which is filled with the measured gas.

The metal shell 11 includes the oxygen sensor 1. The oxygen sensor is fixed to the pipe 19 by screwing the metal shell 11 into the attaching hole 19a. The tip portion of the detecting element 2 is arranged inside the tube.

In addition to this, a first protector 21 and a second protector 23 are attached to the tip portion of the metal shell 11 so as to cover the tip portion of the detecting element 2 at a constant interval.

Plural gas transmitting ports 21a, 23a for introducing the measured gas to the insides of the protectors 21, 23 are formed in the first protector 21 and the second protector 23.

The outer sleeve 13 is formed in a cylindrical shape, and its tip opening portion is externally fitted to be fixed to a portion on the backward side from the step portion 11a located outside the pipe 19.

This outer sleeve 13 accommodates the detecting element 2 therein to protect the detecting element 2 from external water, oil, dust, flied stones, etc.

Further, the outer sleeve 13 stores an insulating separator 27 formed by ceramic in a sleeve shape on the backward side from the detecting element 2.

The separator 27 has a flange portion 27a on its outer circumferential face. The separator 27 is engaged with a convex portion 13a projected to the diametrical inside formed in the outer sleeve 13 by the flange portion 27a. The separator 27 is fixed to a predetermined position within the outer sleeve 13. The separator 27 has plural through holes formed in the axial direction, and stores lead wires 35, 41, 47 introduced from the exterior into these through holes through an outer sleeve cover 30.

An outer sleeve cover 30 includes columnar rubber (e.g., fluoro rubber). The outer sleeve cover 30 is fitted to a rear end opening portion of the outer sleeve 13. The outer sleeve cover has functions as a seal member for protecting the interior of the outer sleeve 13 from water, oil, dust, etc.

Further, the outer sleeve cover 30 has a vent hole 31 extended through the interior of the outer sleeve 13 in the axial direction in the central portion. Further, plural (four in this embodiment) through holes 33 for the lead wires for introducing the lead wires from the exterior into the outer sleeve are formed around this vent hole 31.

Namely, in this oxygen sensor 1, the lead wire 35 electrically connected to the inside electrode 2a of the detecting element 2, the lead wire 41 electrically connected to the outside electrode 2b of the detecting element 2, and the pair of lead wires 47 (one unillustrated lead wire is arranged forward in FIG. 1) connected to the ceramic heater 3 are inserted into the through hole 33 for each lead wire, and are introduced into the separator 27.

Concretely, one lead wire 35 for the detecting element 2 is electrically connected to the inside electrode 2a of the detecting element 2 via a terminal fitting made by a connector portion 36, a drawing portion 37 and a sleeve-shaped internal electrode connecting portion 38 coming in contact with the internal electrode.

Another lead wire 41 is electrically connected to the outside electrode 2b of the detecting element 2 via a terminal fitting made by a connector portion 42, a drawing portion 43 and an external electrode connecting portion 44.

The pair of lead wires 47 for a heater for flowing an electric current through the ceramic heater 3 are connected to a pair of heater terminal portions 48 formed in the rear end portion of the ceramic heater 3 through the outer sleeve cover 30 and the interior of the separator 27. The electric current is flowed to an unillustrated resisting circuit for generating heat and buried into the ceramic heater 3 via this heater terminal portion 48.

The construction of a filter unit 50 fitted and inserted into the vent hole 31 of the outer sleeve cover 30 will next be explained by using FIG. 2.

Figure 2:
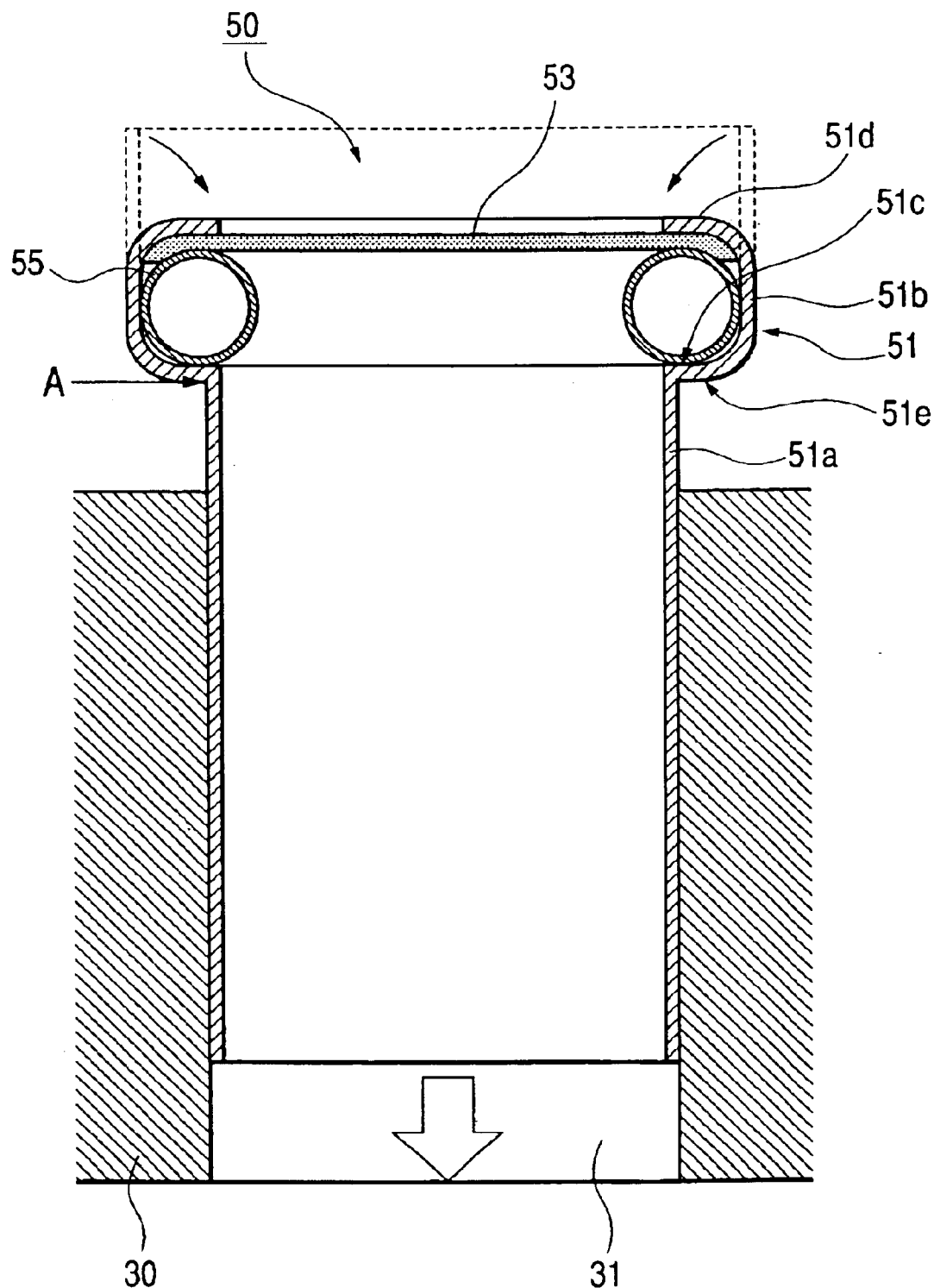
FIG. 2 is a schematic sectional view showing a construction of a filter unit 50.

FIG. 2 is an explanatory view showing an attaching mode of the filter unit 50 into the outer sleeve cover 30. FIG. 2 is also a schematic sectional view along the axial direction of the filter unit 50 before the filter unit 50 is fixed to the outer sleeve cover 30.

The filter unit 50 includes a cylindrical tubular member 51 having an enlarged diameter on a predetermined boundary A, a sheet-shaped filter 53, an O-ring 55 as a seal member, etc.

The tubular member 51 includes a small diameter portion 51a on the forward side from the boundary A (arranged on the metal shell side), and a large diameter portion 51b on the backward side from the boundary A (arranged on the side opposed to the metal shell).

The outside diameter of the small diameter portion 51a is approximately set to the same size as the inside diameter of the vent hole 31 formed in the outer sleeve cover 30.

The axial length of the small diameter portion 51a is approximately set to the same size as the axial length of the outer sleeve cover 30. Further, the tubular member 51 is formed such that a step portion 51c is arranged by the above diametrical enlargement in the inner wall of the tubular member 51 on the boundary A.

On the other hand, the filter 53 includes a permeable filter for preventing the transmission of a liquid such as water (waterdrop, etc.), oil, etc., and allowing the transmission of a gas (air, etc.) and having a water repellent property and an oil repellent property. The filter 53 has a sheet shape and is formed in a disk shape having an outside diameter set to about the same size as the inside diameter of the large diameter portion 51b of the tubular member 51.

Concretely, a member provided by performing oil repellent processing (e.g., oleo processing of goretex) with respect to in a porous fiber structural body of the water repellent property (product name: e.g., goretex (Japan Goretex (Co., Ltd.)) obtained by drawing an unburned molding body of polytetrafluoroethylene (PTFE) in the direction of one axis or more at a heating temperature lower than the melting point of the PTFE is used as the filter 53 of this embodiment.

Here, the oil repellent processing is performed in the filter 53 since there is a case in which the oxygen sensor 1 of this embodiment is used within a vehicle such as an automobile, etc. When the oil is attached to the porous fiber structural body, the surface tension of water attached to the porous fiber structural body is reduced by this attachment.

Therefore, there is a possibility that no water repellent property of the filter can be sufficiently fulfilled. However, when the oil repellent processing is performed in the filter 53 as in this embodiment, the water repellent property of the filter 53 can be sufficiently fulfilled. Accordingly, it is possible to prevent the waterdrop from being transmitted through the filter 53.

In addition to this, a member having an outside diameter approximately conformed to the inside diameter of the large diameter portion 51b of the tubular member 51 is used as the O-ring 55 of the filter unit 50.

The filter unit 50 of this embodiment is made by bending the rear end portion of the large diameter portion 51b and folding this rear end portion (folding portion 51d) in the central direction of the large diameter portion (a small arrow direction of FIG. 2) after the O-ring 55 and the filter 53 are sequentially stored onto the step portion 51c of the tubular member 51 so as to arrange the filter 53 on the upper side.

The filter unit 50 nips and supports the O-ring 55 and the filter 53 by this bending processing between the step portion 51c and the folding portion 51d. Thus, while the O-ring 55 and the filter 53 are fixed in predetermined positions inside the tubular member 51, the filter unit 50 blocks a gap (e.g., the gap between the outer edge of the filter 53 and the inner wall of the tubular member) able to become an invasion port of water, oil, dust, etc. inside the tubular member 51.

In this embodiment, after the filter unit 50 is inserted into the vent hole 31 of the outer sleeve cover 30, the tip of the small diameter portion 51a is bent toward the diametrical outside at the tip of the outer sleeve cover 30 so that the filter unit 50 is fixed to the outer sleeve cover 30.

Figure 3:
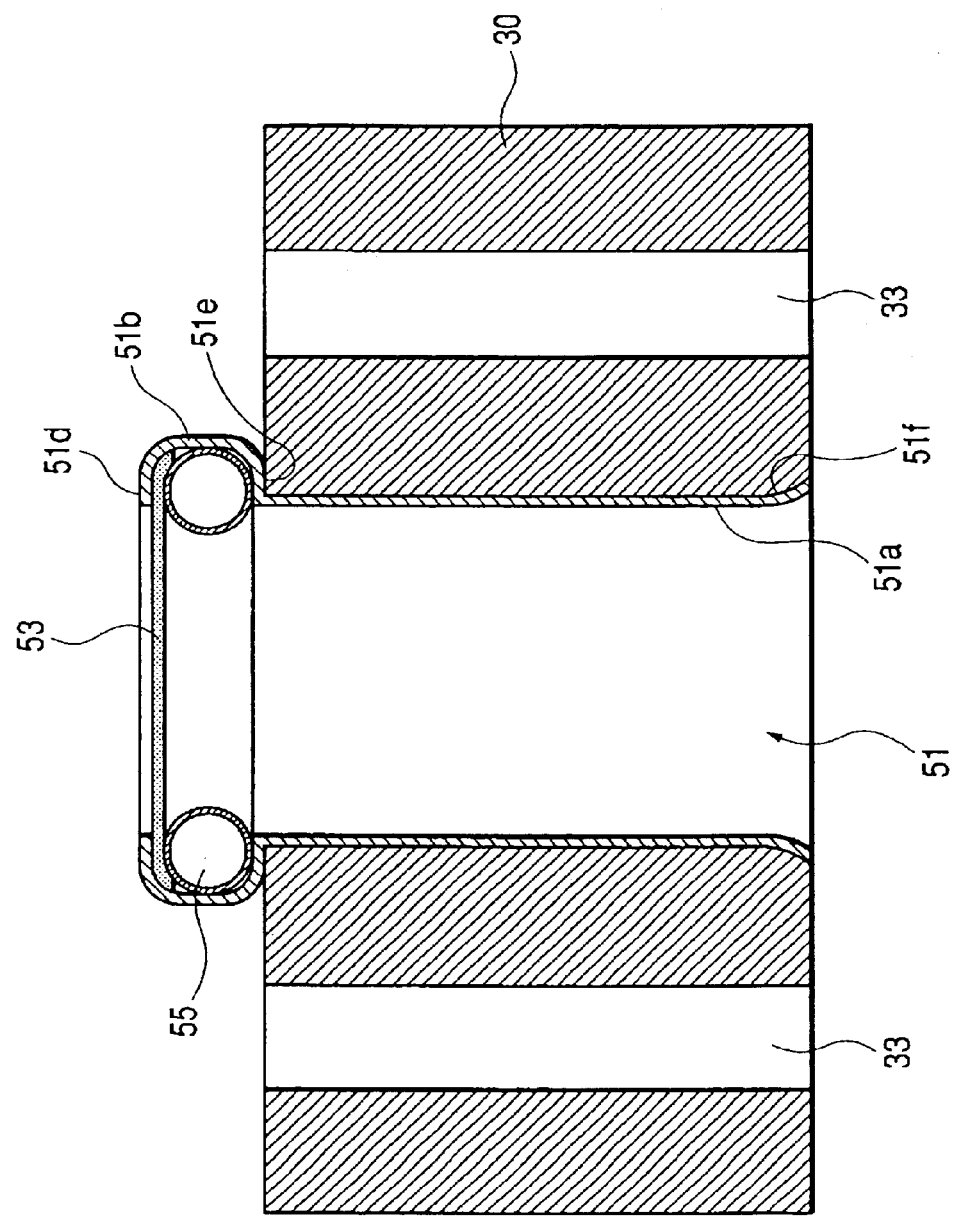
FIG. 3 is a schematic sectional view showing a construction of an outer sleeve cover 30 fitting and inserting the filter unit 50 thereinto.

FIG. 3 is a schematic sectional view of the filter unit 50 and the outer sleeve cover 30 showing the construction of the filter unit 50 after the bending processing.

After this bending processing, the filter unit 50 is engaged with the rear end portion of the outer sleeve cover 30 on the outer face 51e of the step portion 51c (second engaging portion) of the tubular member 51 formed in accordance with a change in diameter on the boundary A. The filter unit 50 is also engaged with the tip portion of the outer sleeve cover 30 by a folding portion 51f (first engaging portion) formed at the tip of the filter unit 50 by the bending processing.

Further, in this embodiment, after the filter unit 50 is fixed to the outer sleeve cover 30 as mentioned above, the outer sleeve cover 30 is fitted to the rear end opening portion of the outer sleeve 13 while each of the lead wires 35, 41, 47 is inserted into each through hole 33 for the lead wire. After the fitting, the side face of the outer sleeve 13 is bent toward the diametrical inside so that its outer sleeve cover 30 is fixed onto the inside of the rear end portion of the outer sleeve 13. Thus, the boundary of the outer sleeve 13 and the outer sleeve cover 30, and the boundary of each lead wire and each through hole 33 for the lead wire in the outer sleeve cover 30 are covered by elasticity of the outer sleeve cover 30 so that the interior of the outer sleeve 13 is water-tightly isolated from the exterior.

Figure 4:
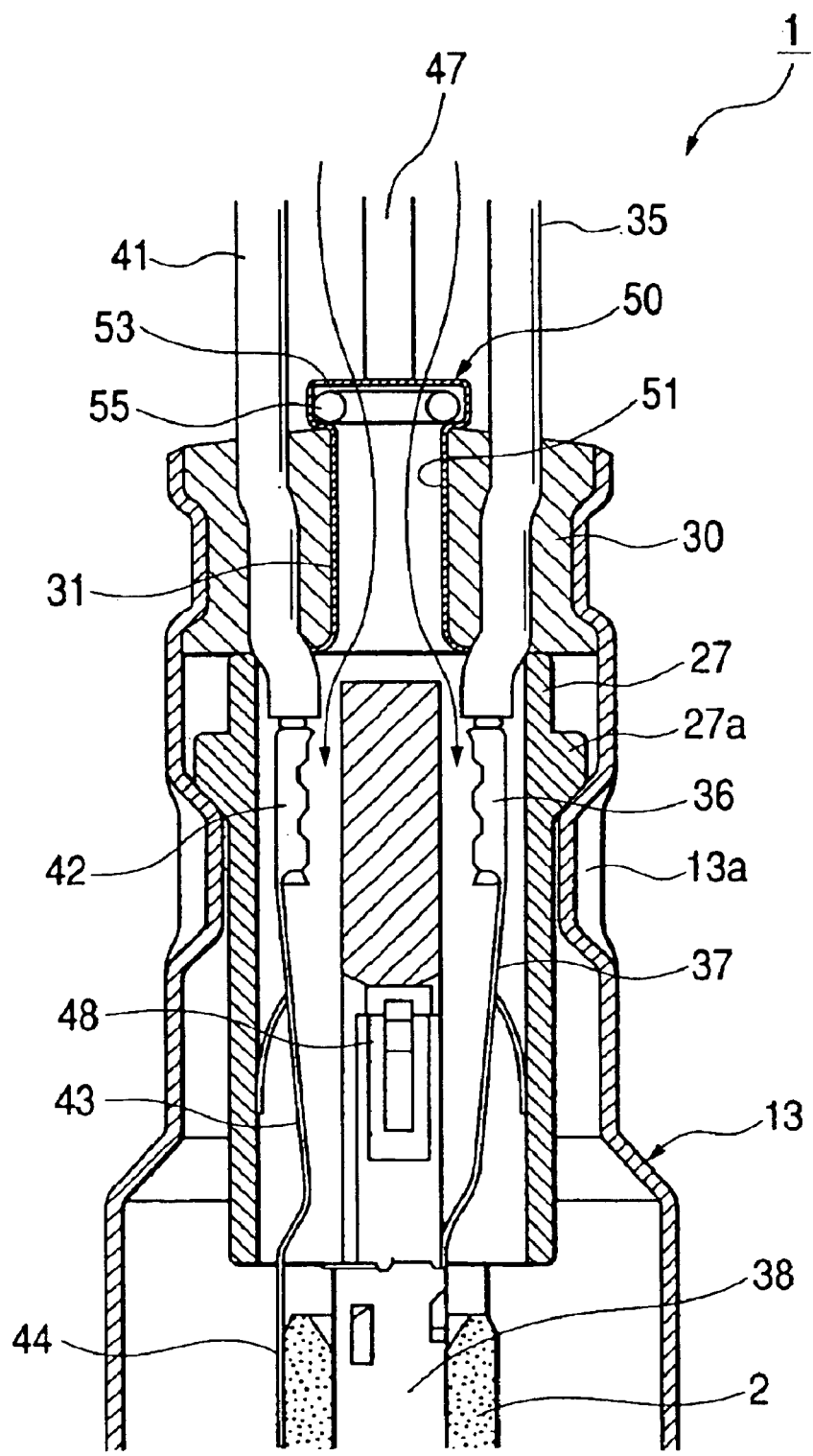
FIG. 4 is a schematic sectional view showing an upper portion construction of the oxygen sensor 1.

On the other hand, the atmosphere as a reference gas required to measure the oxygen concentration of the measured gas is introduced into the outer sleeve 13 as shown by an arrow in FIG. 4 through the filter unit 50 mounted to the vent hole 31, And is supplied to the internal space 2c of the detecting element 2 through the gap between the inner wall of the detecting element 2 and the ceramic heater 3. FIG. 4 is a schematic sectional view enlargedly showing the upper portion of the oxygen sensor 1.

In the above description, the oxygen sensor 1 of the first embodiment has been explained. However, in this oxygen sensor 1, the filter unit 50 having the filter 53 fixed to the inside of the tubular member 51 in advance is formed as a separate body, and the vent hole 31 is then covered by the filter 53 in the method for fitting and inserting the filter unit 50 into the vent hole 31. Therefore, the oxygen sensor 1 has a construction in which the filter is inserted into the vent hole 31 while the filter is arranged outside the insertion member as in the conventional case. Therefore, it is possible to dissolve the problem that the filter is broken. Further, since the oxygen sensor 1 is simply mounted, productivity of the oxygen sensor 1 can be improved.

There are various types in which the gas sensor has five lead wires, etc. However, when the filter unit 50 is separately manufactured as in the first embodiment, the filter unit 50 can be easily applied to such gas sensors if the size of the vent hole 31 is fitted even in the gas sensors of different types. Accordingly, manufacture cost of the gas sensor can be restrained if the method for fitting and inserting the filter unit 50 into the vent hole 31 as in the first embodiment is adopted.

In addition to this, the first embodiment adopts the method for fixing the filter 53 within the large diameter portion 51b of the tubular member 51 by nipping and supporting the filter 53 by the elastic force of the O-ring 55 between the folding portion 51d and the step portion 51c.

Therefore, the filter 53 can be firmly fixed into the tubular member 51 so as to block the vent hole 31 by approximately setting the diameter of the filter 53 to be slightly greater than that of the vent hole 31. Accordingly, in the oxygen sensor 1 of this embodiment, the using amount of the expensive filter 53 can be restrained and manufacture cost of the oxygen sensor 1 can be restrained.

In the first embodiment, the O-ring 55 plays a role for preventing the invasion of a waterdrop, etc. from the outer edge side of the filter 53. Therefore, the interior of the filter unit 50 can be water-tightly maintained so that the interior of the outer sleeve 13 can be protected from the waterdrop, oil, dust, etc. for a long period.

Further, in the oxygen sensor 1, since the filter unit 50 is firmly fixed to the outer sleeve cover 30 by the outer face 51e of the step portion 51c and the folding portion 51f, it is possible to sufficiently restrain the filter unit 50 from falling out of the outer sleeve cover 30.

In addition to this, in the oxygen sensor 1, the large diameter portion 51b is arranged outside the backward side from the vent hole 31. Therefore, no dust is easily collected in the vicinity of the filter 53 within the large diameter portion 51b, which is convenient. Namely, in this oxygen sensor 1, it is possible to prevent the permeable property of the filter 53 from becoming worse by accumulating the dust.

The construction of a main portion of an oxygen sensor 61 of a second embodiment will next be explained with reference to FIG. 5.

Figure 5:
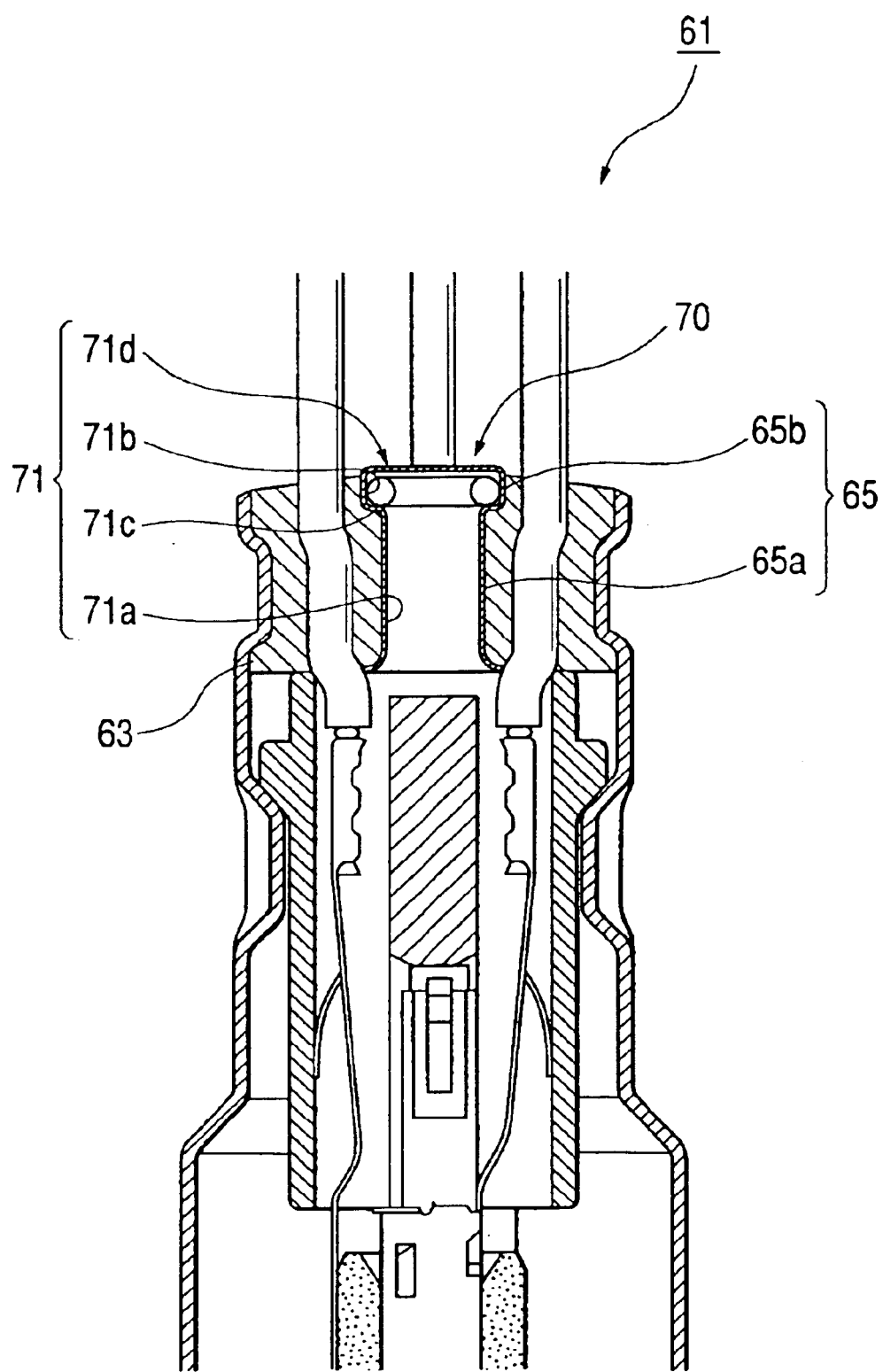
FIG. 5 is a schematic sectional view showing the upper portion construction of an oxygen sensor 61 of a second embodiment.

FIG. 5 is a sectional view schematically showing an upper portion construction of the oxygen sensor 61 of the second embodiment. In the following explanation, a portion different in construction from the oxygen sensor 1 of the first embodiment will be described and the explanation of each portion of the same construction is omitted.

As shown in FIG. 5, in the oxygen sensor 61 of the second embodiment, the axial length of a filter unit 70 is approximately set to the same as the axial length of an outer sleeve cover 63. The diameter of a vent hole 65 of the outer sleeve cover 63 is enlarged upward from a predetermined boundary in conformity with the outer shape of the filter unit 70. A large diameter portion 71b of a tubular member 71 is stored into the vent hole 65 as well as a small diameter portion 71a of the tubular member 71.

Namely, in the second embodiment, the vent hole 65 of the outer sleeve cover 63 includes a large diameter portion 65b having an inside diameter set to about the same size as the outside diameter of the large diameter portion 71b of the tubular member 71, and a small diameter portion 65a having an inside diameter set to about the same size as the outside diameter of the small diameter portion 71a of the tubular member 71.

The tubular member 71 of the filter unit 70 includes the large diameter portion 71b of a size fitted to the large diameter portion 65b of the vent hole 65, and the small diameter portion 71a of a size fitted to the small diameter portion 65a of the vent hole 65.

The filter unit 70 is formed such that the O-ring 55 and the filter 53 are stored inside the large diameter portion 71b located between a folding portion 71d formed at the upper end by bending processing and a step portion 71c formed on the boundary of the large diameter portion 71b and the small diameter portion 71a.

The filter unit 70 is fitted and inserted from the rear end side of the outer sleeve cover 63 into the vent hole 65. After this fitting insertion, the tip portion of the filter unit 70 is bent toward the diametrical outside of the vent hole 65, and is fixed to the outer sleeve cover 63. In this state, the filter 53 is approximately fixed in the same position as the rear end face of the outer sleeve cover 63.

The oxygen sensor 61 in the second embodiment explained above is formed such that the entire filter unit 70 is approximately stored in the vent hole 65. Therefore, in accordance with this oxygen sensor 61, it is possible to dissolve that the filter unit 70 is projected from the outer sleeve cover 63. Accordingly, the oxygen sensor 61 can be made compact.

Figure 6:
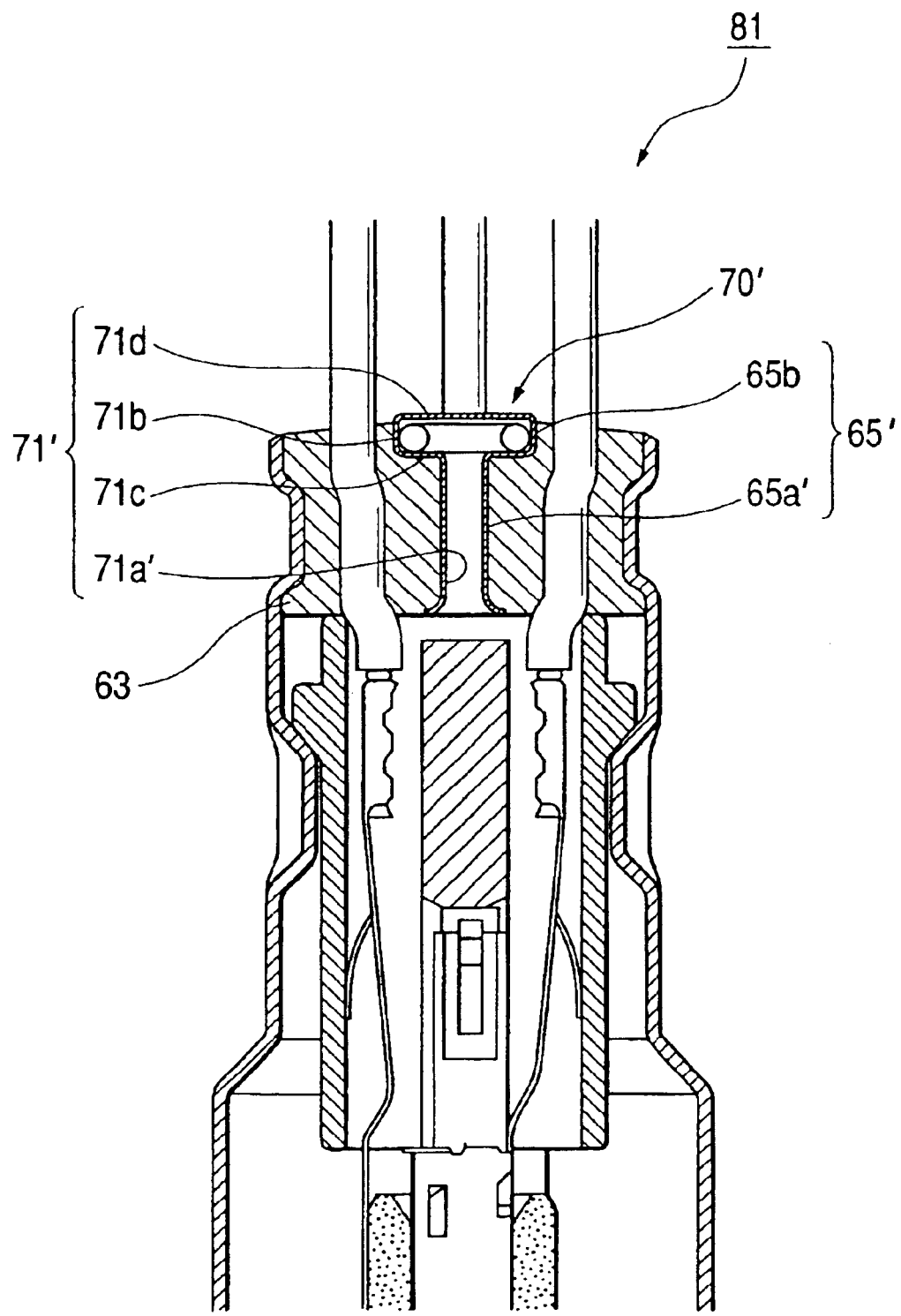
FIG. 6 is a schematic sectional view showing the upper portion construction of an oxygen sensor 61'.

In addition to this, the oxygen sensor 61 in the second embodiment can be deformed as in an oxygen sensor 81 shown in FIG. 6. FIG. 6 is an explanatory view schematically showing the construction of a main portion of the oxygen sensor 81.

In the oxygen sensor 81 shown in FIG. 6, the diameter of a vent hole small diameter portion 65a of the oxygen sensor 61 of the above second embodiment is reduced (a small diameter portion 65a' of a vent hole 65'), and the diameter of a small diameter portion 71a of the filter unit 70 is reduced (a small diameter portion 71a' of a tubular member 71') in conformity with this reduction.

As can be seen from this modified example, in the filter unit 70' of the above construction, even when the vent hole small diameter portion 65a' of the outer sleeve cover 63 is small, the size of the filter 53 can be set to a large size as it is. Accordingly, it is possible to restrain the venting amount of a reference gas from becoming worse by reducing the vent hole small diameter portion 65a' to a certain extent. In other words, the venting amount can be still secured even when the vent hole is reduced in size.

Accordingly, when such a filter unit 70' is used, the size of the vent hole 65' can be freely set in comparison with the conventional case in a design process of the oxygen sensor 81.

As mentioned above, the first engaging portion of the filter unit in the gas sensor of the present invention corresponds to the folding portion 51f of the filter unit 50, and the second engaging portion corresponds to the outer face 51e of the step portion 51c of the filter unit 50.

The gas sensor of the present invention is not limited to the above embodiments, but various modes can be adopted.

For example, in the above embodiments, the filter 53 is arranged inside the tubular member 51 on the backward side of the outer sleeve cover 30, but may be also arranged on the forward (tip) side of the outer sleeve cover 30.

In addition to this, in this embodiment, only one O-ring 55 is arranged within each of the filter units 50, 70, 70'. However, for example, the O-ring may be also arranged on each of the step portion 51c side and the pair of O-rings within the large diameter portion 51b may further nip the folding portion 51d side, and the filter 53. In accordance with such a construction, the seal property of the filter units 50, 70, 70' can be further raised.

Figure 10:
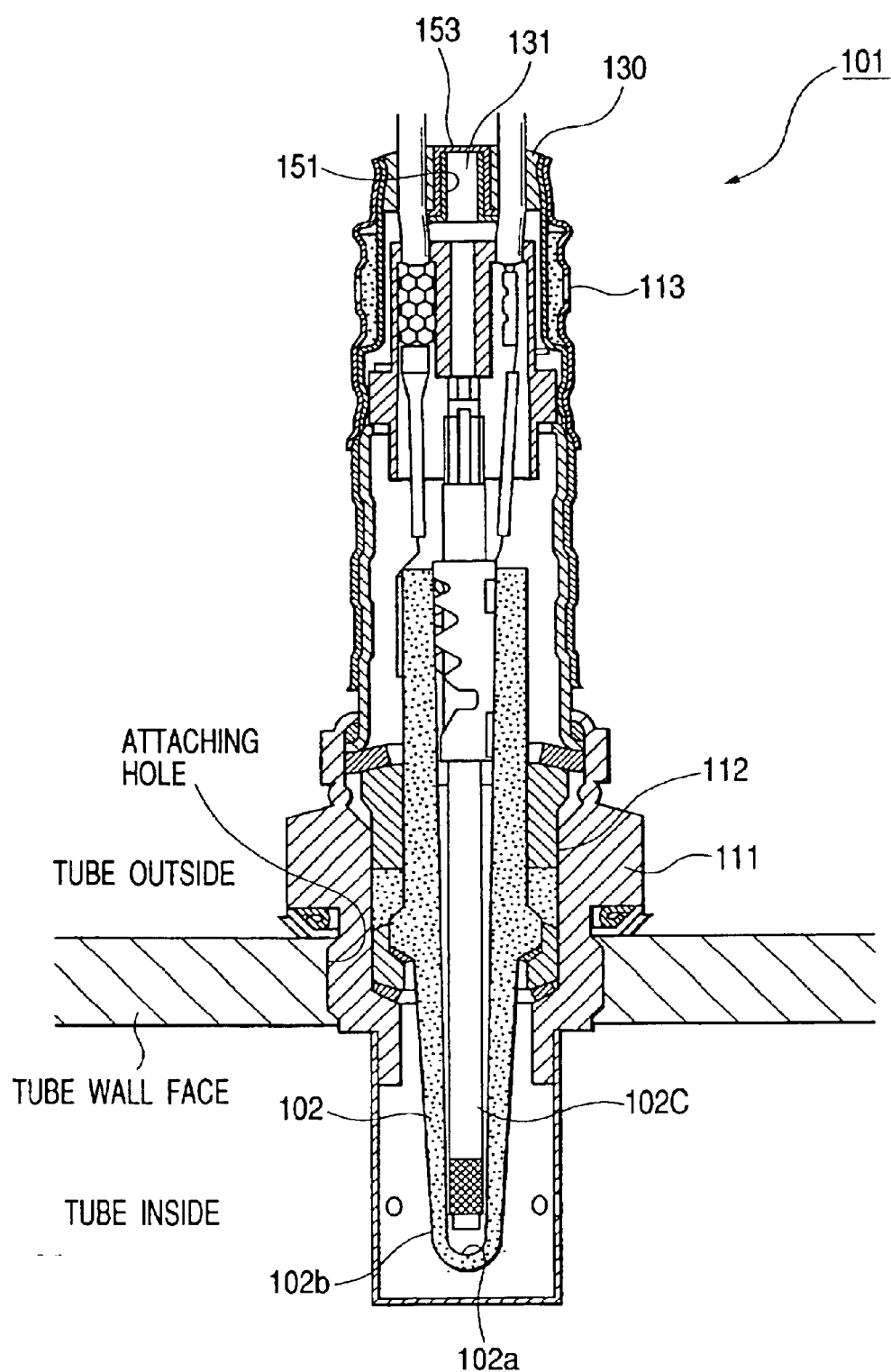
FIG. 10 is a sectional view showing the construction of a conventional oxygen sensor 101.
Figure 11:
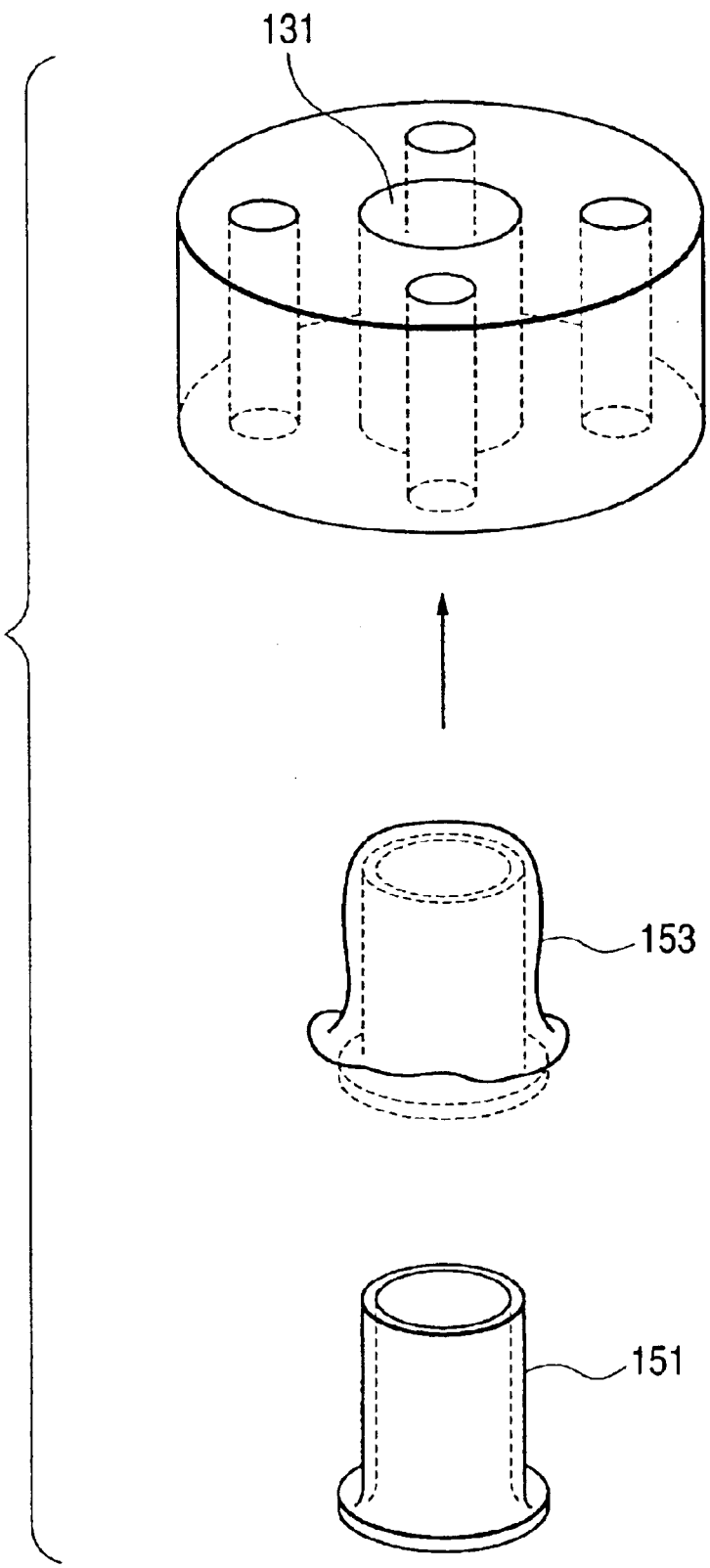
FIG. 11 is an explanatory view showing the attaching mode of a filter 153 in the conventional oxygen sensor 101.

The present invention can be also applied to the conventional oxygen sensor 101 shown in FIG. 10.

Further, in this embodiment, the detecting element 2 is set to a cylindrical body of a hollow shaft shape having a bottom and closed at its tip. However, it is also possible to use a type in which a pair of electrodes is formed on the surface of a solid electrolytic body of an oxygen ion conductive property formed in a plate shape. In addition to this, a detecting element having a plate-shaped ceramic heater arranged integrally with the oxygen ion conductive property solid electrolytic body of the plate shape forming the pair of electrodes therein may be also used.

Figure 7:
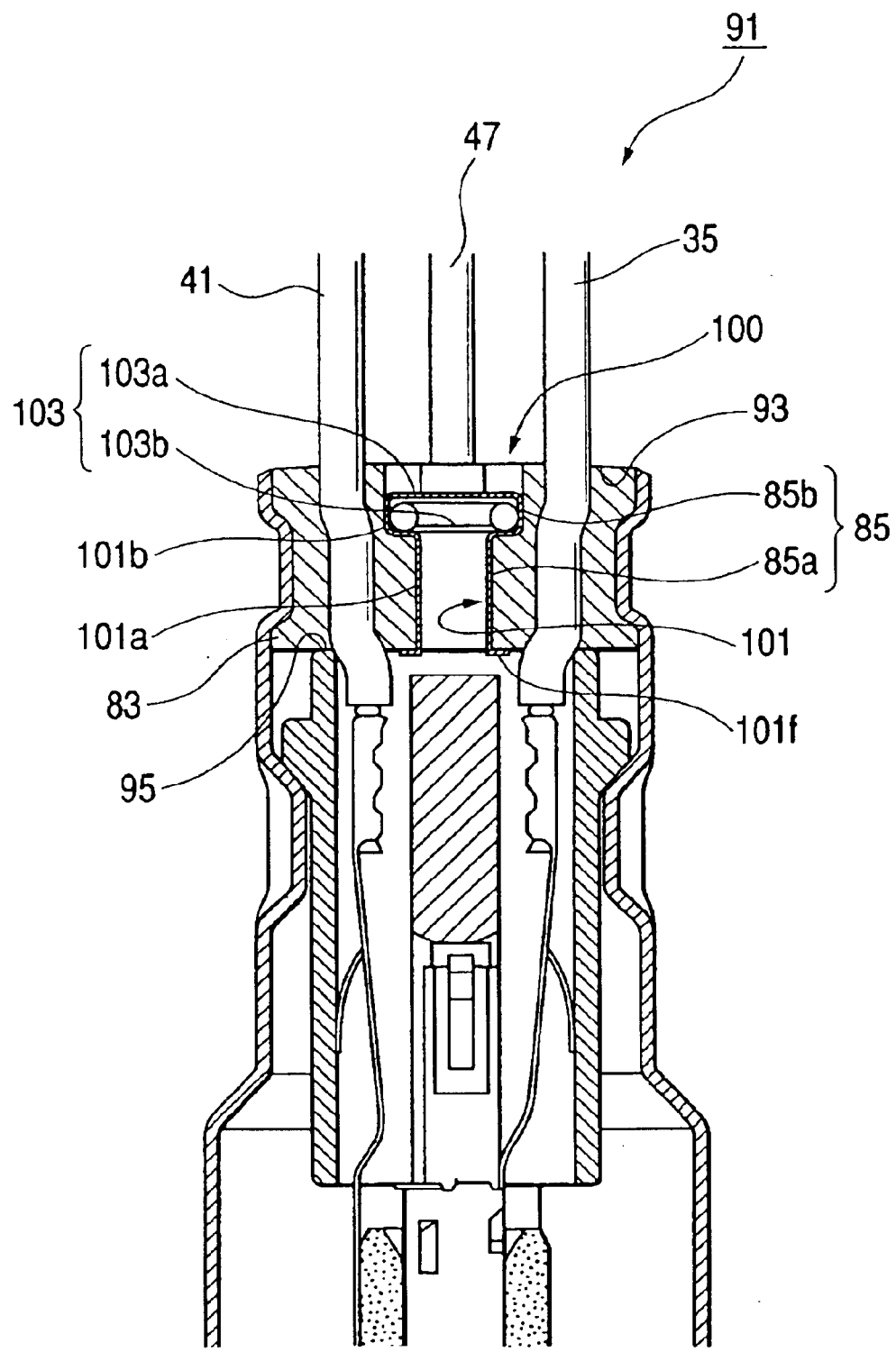
FIG. 7 is a schematic sectional view showing the upper portion construction of an oxygen sensor 91 of a third embodiment.
Figure 8A:
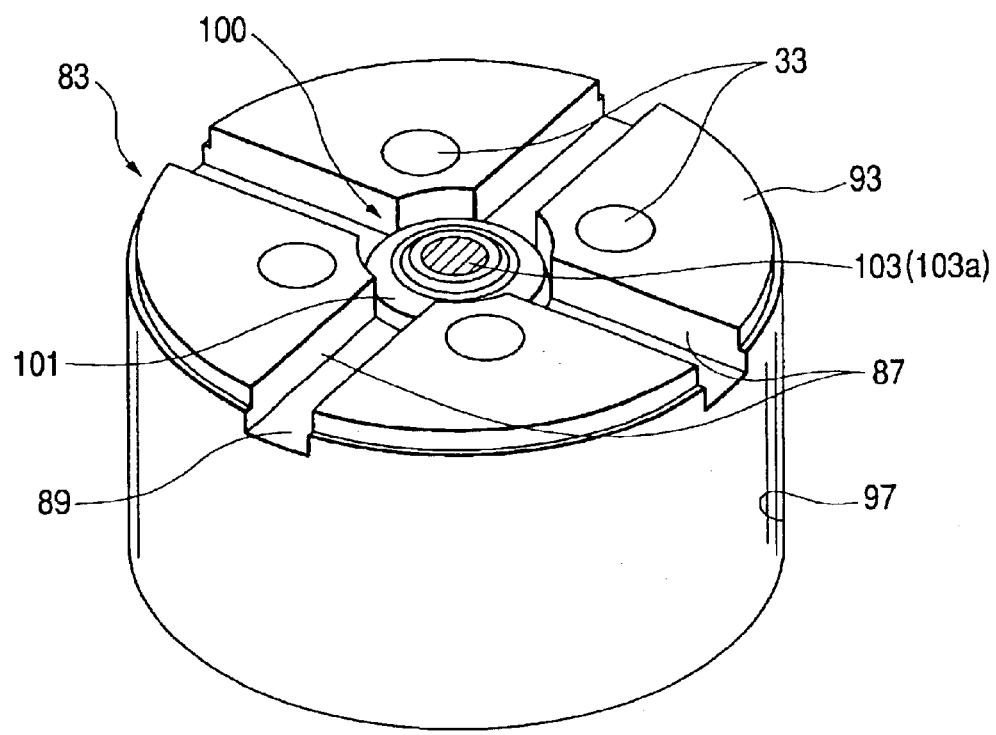
FIG. 8A is a perspective view seen from the rear end face 93 side of an outer sleeve cover 83 fitting and inserting a filter unit 100 thereinto.
Figure 8B:
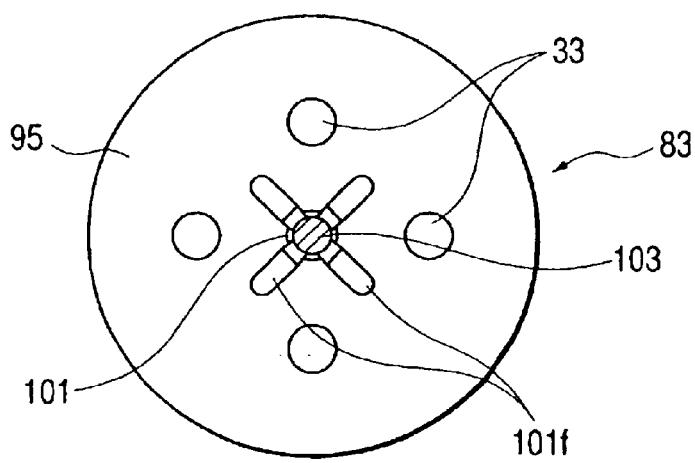
FIG. 8B is a plan view seen from the tip face 95 of the outer sleeve cover 83 fitting and inserting the filter unit 100 thereinto.

Further, an oxygen sensor 91 of a third embodiment will be explained with reference to FIGS. 7 and 8. FIG. 7 is a sectional view schematically showing an upper portion structure of the oxygen sensor 91 of the third embodiment. FIG. 8(a) is a perspective view in which an outer sleeve cover 83 having a filter unit 100 is seen from the side of a rear end face 93 in the oxygen sensor 91 of the third embodiment. FIG. 8(b) is a plan view in which the outer sleeve cover 83 having the filter unit 100 is seen from the side of a tip face 95. In the following explanation, portions different from the oxygen sensors 1, 61 of the first and second embodiments will be described and the explanation of each portion of the same construction is omitted.

As shown in FIG. 7, in the oxygen sensor 91 of the third embodiment, the axial length of the filter unit 100 is set to be shorter than that of the outer sleeve cover 83, and the diameter of a vent hole 85 of the outer sleeve cover 83 is enlarged upward from a predetermined boundary in conformity with the outer shape of the filter unit 100 so that a large diameter portion 101b of a tubular member 101 is stored into the vent hole 85 as well as a small diameter portion 101a of the tubular member 101.

Namely, in the third embodiment, the vent hole 85 of the outer sleeve cover 83 includes a large diameter portion 85b having an inside diameter set to about the same size as the outside diameter of the large diameter portion 101b of the tubular member 101, and a small diameter portion 85a having an inside diameter set to about the same size as the outside diameter of the small diameter portion 101a of the tubular member 101. The axial length of the large diameter portion 85b of the vent hole 85 is set to be greater than that of the large diameter portion 101b of the tubular member 101. The upper face (a face located on the upper side in FIG. 7) of a filter 103 of the filter unit 100 is arranged on the forward side from the rear end face 93 of the outer sleeve cover 83.

In this third embodiment, a folding portion 101f formed at the tip of the filter unit 100 (tubular member 101) and engaged with the tip portion of the outer sleeve cover 83 is different from that in each of the first and second embodiments. Namely, in the first and second embodiments, the folding portion 51f is formed so as to enlarge the diameter of the tip side of the tubular member 51 toward the diametrical outside. In contrast to this, in this third embodiment, as shown in FIG. 8(b), when the folding portion is folded toward the diametrical outside on the tip side of the tubular member 101, the folding portion 101f formed in a cross shape and engaged with the tip portion (tip face 95) of the outer sleeve cover 83 is formed on the tip side of the tubular member 101.

The filter unit 100 having such a construction is fitted and inserted from the rear end side of the outer sleeve cover 83 into the vent hole 85. After this fitting insertion, four folding portions 101f located on the tip side of the tubular member 101 are folded so as to form the cross shape toward the diametrical outside so that the filter unit 100 is fixed to the outer sleeve cover 83.

Further, in the third embodiment, as shown in FIG. 8(a), plural groove portions 87 are formed in a cross shape in positions not interfering with through holes 33 for lead wires on the rear end face 93 of the outer sleeve cover 83. In each of the groove portions 87, one end side (inside) of the groove portion is communicated with the vent hole 85, and the other end side (outside) is opened to a sidewall face 97 of the outer sleeve cover 83. The filter 103 is arranged so as to be located on the rear end side from a deepest portion 89 of this groove portion 87. Namely, in the oxygen sensor 91 of this third embodiment, as mentioned above, the upper face of the filter 103 in the filter unit 100 has a shape arranged on the forward side from the rear end face 93 of the outer sleeve cover 83. Therefore, damage of the filter 103 due to flied stones, etc. can be effectively restrained. Further, even when water, etc. are splashed onto the upper face of the filter 103, this water can be discharged on the diametrical outside of the outer sleeve cover 83 through the groove portion 87.

Accordingly, since the oxygen sensor 91 in this third embodiment has the filter unit 100 having the filter 103 arranged on the forward side from the rear end face 93 of the outer sleeve cover 83, it is possible to effectively restrain the filter 103 from being damaged by flied stones, etc. Further, since the above groove portion 87 is formed on the rear end face 93 of the outer sleeve cover 83, it is possible to effectively restrain water, dust, etc. from being collected on the upper face of the filter 103 even when the filter 103 is arranged on the forward side from the rear end face 93 of the outer sleeve cover 83.

In the third embodiment, the filter 103 includes plural (two) filters made by a first filter 103a and a second filter 103b, and includes arranging these plural filters 103a, 103b inside the tubular member 101. Concretely, the filters 103a, 103b are oppositely arranged inside the tubular member 101 through the O-ring 55. These filters 103a, 103b, and the O-ring 55 are nipped and supported between the step portion 51c and the folding portion 101d. Thus, the invasion of water, oil, etc. can be more reliably prevented by doubly arranging the filter 103. Further, if one filter is damaged, a filter function using the other filter can be obtained by doubly arranging the filter 103. The two filters 103a, 103b may have the same performance, and may also have divisional functions by using a filter having a water repellent property on one side and a filter having an oil repellent property on the other side, etc.

Figure 9A:
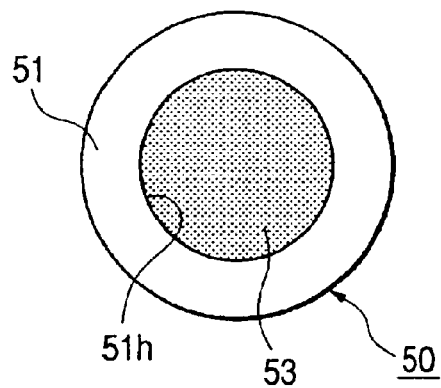
FIG. 9A is an explanatory view showing first modified example in which a partition plate is arranged on the rear end side of a filter in the filter unit.
Figure 9B:
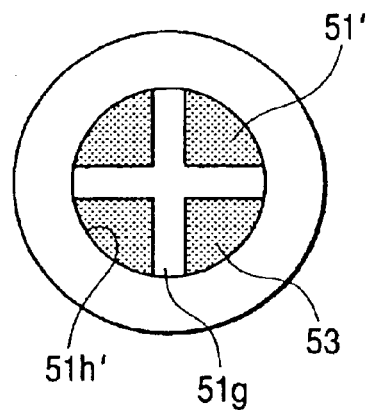
FIG. 9B is an explanatory view showing second modified example in which a partition plate is arranged on the rear end side of a filter in the filter unit.
Figure 9C:
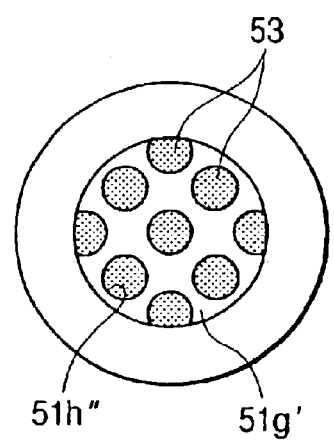
FIG. 9C is an explanatory view showing third modified example in which a partition plate is arranged on the rear end side of a filter in the filter unit.

Modified examples for preventing the damage of the filter will be further explained with reference to FIG. 9. FIG. 9(a) is a plan view in which the filter unit 50 of the above first embodiment is seen from the rear end side. The tubular member 51 has one opening portion 51h, and a filter 53 attached into the tubular member 51 is exposed from the opening portion 51h. In contrast to this, in the modified examples shown in FIGS. 9(b) and 9(c), the opening portion 51h is divided into plural opening portions 51h', 51h''. The opening area of one opening portion can be reduced by arranging partition plates 51g, 51g' having the plural opening portions 51h', 51h'' inside the tubular member 51 in a state in which these partition plates 51g, 51g' are arranged on the rear end side of the filter 53. Accordingly, it is possible to effectively prevent the filter 53 from being damaged by flied stones, etc. It is also possible to adopt a structure formed by knitting a wire material of a metal, etc. in a mesh shape as a form of the partition plate.

In addition to this, in this embodiment, the oxygen sensor 1 for introducing the atmosphere as a reference gas of the detecting element 2 from the vent hole 31 of the outer sleeve cover 30 into the outer sleeve 13 is illustrated. However, the present invention may be also applied in a gas sensor able to detect the gas concentration without introducing the atmosphere into the outer sleeve 13.

For example, when the gas sensor is attached to an exhaust pipe of an internal combustion engine, this sensor is used in an environment at high temperature. Therefore, a corrosive gas is generated from the outer sleeve cover (particularly, the outer sleeve cover manufactured by fluoro rubber) arranged in a rear end opening portion of the outer sleeve by a thermal factor of this sensor. It is considered that there is a possibility that each portion of the sensor stored into the outer sleeve is corroded by this corrosive gas. Accordingly, in such a gas sensor, a function for effectively flowing-out this corrosive gas to the exterior is obtained by arranging the vent hole as a circulating path of the gas of the interior and the exterior of the outer sleeve in the outer sleeve cover. However, if the vent hole is formed in the outer sleeve cover in this way, it is naturally necessary to prevent the invasion of a waterdrop, etc. while the circulation of the gas is allowed within the outer sleeve. Therefore, it is possible to obtain a gas sensor in which the above function can be simply and cheaply attained by adopting the present invention.

Further, in the above first and second embodiments, one filter 53 is arranged inside the tubular member 51 as an example, but plural filters 53 may be also overlapped or fixedly arranged inside the tubular member 51 at a predetermined interval with respect to the central axis direction of the tubular member 51. In accordance with such a construction, if the filter of an outermost layer exposed to the exterior of the gas sensor is broken, waterproof property can be maintained by the other filters. As a result, reliability of the gas sensor can be raised.

What is claimed is:

1. A gas sensor comprising:
   a detecting element including a pair of electrodes which are formed on a surface of a solid electrolytic body of an oxygen ion conductive property;
   a metal shell including a through hole in an axial direction of said metal shell, said metal shell holding said detecting element within said through hole so as to expose a tip portion of said detecting element to a measured gas from a tip side of said through hole;
   an outer sleeve provided on a rear end side of said metal shell, said outer sleeve internally accommodating said detecting element; and
   an outer sleeve cover disposed in a rear end opening portion of said outer sleeve, said outer sleeve cover including a vent hole extending from a rear end face of said outer sleeve cover to a tip face of said outer sleeve cover, as a gas flowing path from exterior of said outer sleeve to interior of said outer sleeve,
   wherein said outer sleeve cover includes a filter unit including a tubular member and a filter, and
   wherein said tubular member is disposed in said vent hole of said outer sleeve cover, and
   wherein said filter is disposed in said tubular member and has a permeable property and a water repellent property for covering said vent hole.

2. The gas sensor according to claim 1, wherein said tubular member has a first engaging portion engaged with a tip portion of said outer sleeve cover, and a second engaging portion engaged with a rear end portion of said outer sleeve cover.

3. The gas sensor according to claim 1, wherein said filter is fixed to said tubular member at a portion projecting from the rear end face of said outer sleeve cover.

4. The gas sensor according to claim 1, wherein said filter is fixed to said tubular member at a portion disposed within said vent hole of said outer sleeve cover.

5. The gas sensor according to claim 4, wherein a groove portion formed in said rear end face of said outer sleeve cover has one end side communicated with said vent hole, and other end side of said groove portion opened to a side wall face of said outer sleeve cover, and wherein said filter is disposed in said tubular member at a position between a deepest portion of said groove portion and a groove opening at an outermost surface of said rear end face.

6. The gas sensor according to claim 5, wherein said outer sleeve cover includes a plurality of through holes, and said sensor further comprises a plurality of lead wires passing through said through holes and electrically connected to said detecting element, and wherein said groove portion is formed on said rear end face of said outer sleeve cover except for where said through holes for said lead wire are formed.

7. The gas sensor according to claim 1, wherein said filter has an oil repellent property.

8. The gas sensor according to claim 1, wherein said filter unit includes plural filters, which are fixed to an inside of said tubular member.

9. The gas sensor according to claim 1, wherein said filter unit includes a partition plate having plural opening portions for exposing said filter inside said tubular member, and wherein said partition plate is fixed to a rear end side of the filter.

10. The gas sensor according to claim 1, wherein said filter unit includes a seal member for water-tightly fixing said filter inside said tubular member.

11. The gas sensor according to claim 10, wherein said tubular member includes a filter fixing portion for fixing said filter in a predetermined position inside of said tubular member, and wherein said filter unit includes said filter and an O-ring as said seal member, which are fixedly nipped and supported between said filter fixing portion and an end portion of said tubular member folded in an inside direction of said tubular member.

12. The gas sensor according to claim 11, wherein
   said filter fixing portion includes a folding end portion folded towards a center of said tubular member, a step portion disposed at an opening of said vent hole of said outer sleeve cover, and a large diameter portion disposed between said folding portion and said step portion, and
   wherein said filter is disposed to overlap said O-ring, and
   wherein said O-ring and said filter are fixedly nipped and supported within said large diameter portion between said step portion and the folding portion.

* * * * *